United States Patent
Heindl et al.

(10) Patent No.: US 10,526,536 B2
(45) Date of Patent: Jan. 7, 2020

(54) COMPOSITIONS WITH THERMOLABILE DYES

(71) Applicant: Roche Molecular Systems, Inc., Pleasanton, CA (US)

(72) Inventors: Dieter Heindl, Munich (DE); Hannes Kirzinger, Puergen (DE); Thomas Meier, Munich (DE); Christopher Nelson, Redwood City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 16/063,660

(22) PCT Filed: Dec. 22, 2016

(86) PCT No.: PCT/EP2016/082391
§ 371 (c)(1),
(2) Date: Jun. 18, 2018

(87) PCT Pub. No.: WO2017/109077
PCT Pub. Date: Jun. 29, 2017

(65) Prior Publication Data
US 2018/0371314 A1      Dec. 27, 2018

Related U.S. Application Data

(60) Provisional application No. 62/271,211, filed on Dec. 22, 2015.

(51) Int. Cl.
*C12Q 1/686* (2018.01)
*C09K 11/07* (2006.01)
*C12Q 1/6806* (2018.01)

(52) U.S. Cl.
CPC ............. *C09K 11/07* (2013.01); *C12Q 1/686* (2013.01); *C12Q 1/6806* (2013.01); *C12Q 2527/101* (2013.01); *C12Q 2531/113* (2013.01); *C12Q 2563/107* (2013.01); *C12Q 2563/119* (2013.01)

(58) Field of Classification Search
CPC ..... C12Q 1/686; C12N 9/1241; C12N 9/1275
See application file for complete search history.

(56) References Cited

FOREIGN PATENT DOCUMENTS

| WO | 2008052742 A1 | 5/2008 |
|---|---|---|
| WO | 2009116984 A2 | 9/2009 |
| WO | 2011039425 A1 | 4/2011 |
| WO | 2012083235 A1 | 6/2012 |
| WO | 2015054396 A1 | 4/2015 |
| WO | PCT/EP2016/082391 | 3/2017 |

OTHER PUBLICATIONS

Arata et al. 2008; Millisecond denaturation dynatmics of fluourescent protein revealed by femtoliter container on micro-thermodvice. Lab Chip. 8: 1436-1440.*
Wikipedia. Taq Polymerase on the web at en.wikipedia.org/wiki/Taq_polymerase, 2019.*
Gudnason, H. et al, Comparison of multiple DNA dyes for real-time PCR: effects of dye concentration and sequence composition on DNA amplification and melting temperature, Nucleic Acids Research, (2007), e127-e127, vol. 35.
Mitra K. et al, Rational design of 'water-soluble' bacteriorhodopsin variants, Protein Engineering, (2002), pp. 485-492, vol. 15.
Naser Aliye, et al, Engineering color variants of green fluorescent protein (GFP) for thermostability, pH-sensitivity, and improved folding kinetics, Appl Microbiol Biotechnol, (2015), pp. 1205-1216, vol. 99, Springer, Berlin Heidelberg.
Natta Tansila, et al, Rational Design of Analyte Channels of the Green Fluorescent Protein for Biosensor Applications, Int J Biol Sci, (2007), pp. 463-470, vol. 3, Ivyspring International Publisher.
Sample, V. et al, The structure and function of fluorescent proteins, Chemical Society Reviews, (2009), pp. 2852-2864, vol. 38.
Verkhusha, V. V. et al, The molecular properties and applications of Anthozoa fluorescent proteins and chromoproteins, Nature Biotechnology, (2004), pp. 289-296, vol. 22.
Zheng Cao, et al, Thermodynamic stability of bacteriorhodopsin mutants measured relative to the bacterioopsin unfolded state, Biochimica et Biophysica Acta, (2012), pp. 1049-1054, vol. 1818.

* cited by examiner

*Primary Examiner* — Karen Cochrane Carlson
(74) *Attorney, Agent, or Firm* — Carol Pamela Johns; Jennifer K. Rosenfield

(57) ABSTRACT

The present disclosure provides an aqueous composition comprising a purified thermostable polypeptide with biological activity, and a purified thermolabile water-soluble substance which in a functional conformation at a permissive temperature absorbs light and/or exhibits fluorescence, wherein the maximal permissive temperature of the polypeptide is above the maximal permissive temperature of the substance. The present disclosure further provides methods employing such a composition, and kits containing ingredients to form such a composition.

7 Claims, 3 Drawing Sheets

COMPOSITIONS WITH THERMOLABILE DYES

CROSS-REFERENCE TO RELATED APPLICATIONS

This patent application claims priority to U.S. Provisional Patent Application No. 62/271,211, filed Dec. 22, 2015, and is a national phase application of PCT/EP2016/082391, filed Dec. 22, 2016, the disclosures of which are incorporated by reference herein in their entireties.

The present disclosure provides an aqueous composition comprising a purified thermostable polypeptide with biological activity, and a purified thermolabile water-soluble substance which in a functional conformation at a permissive temperature absorbs light and/or exhibits fluorescence, wherein the maximal permissive temperature of the polypeptide is above the maximal permissive temperature of the substance. The present disclosure further provides methods employing such a composition, and kits containing ingredients to form such a composition.

BACKGROUND OF THE INVENTION

The present disclosure is directed to means useful in processes of setting up and processing biochemical or molecular biological reactions, and monitoring the status thereof. The preparatory work with respect to a biochemical or molecular biological reaction particularly comprises steps of assembling all necessary reactants of a desired reaction. Typically, a biochemical or molecular biological reaction occurs in aqueous solution. Thus, the different reactants are firstly provided as separate components. They have to be combined to form a reaction mixture, i.e. to form a composition with selected ingredients in prescribed concentrations and under defined other conditions, in order to later on allow the desired reaction to take place. The components are mixed to form the desired composition in aqueous solution. To this end, components can be added to the mixture as dry substances or as already dissolved matter. Also, several components can separately be put together, dissolved and mixed to form a reagent, and several reagents can then be combined and mixed in order to form the desired composition (reaction mixture) for the desired reaction.

Reaction mixtures are typically combined from different aqueous solutions with no obvious (e.g. visible) distinctive features. The skilled person is therefore confronted with the task of carefully monitoring the process of assembling in a reaction vessel or plurality of reaction vessels all the necessary reactants (components, component solutions) of the desired reaction mixture. For example, a skilled lab operator relies on information provided by the markings of the container in which a particular reagent stock is provided. But once a reagent is removed from the container and transferred into the reaction vessel, the physical connection of the reagent and the respective marking is lost. Without any further tracking measures the knowledge about presence and identity of the respective reagent in the reaction vessel is lost. In this context a tracking measure can be a specific record indicating that transfer of an aliquot of a particular reagent stock has been made into a particular reaction vessel. Another example for a tracking measure is a colorant that is present in a particular reagent and that can be identified by optical means such as visual inspection. Once the reagent with the colorant has been added to a reaction vessel, the colorant indicates the presence of the respective reagent in the vessel. This principle is already being used in biochemistry and molecular biology, particularly in applications making use of the polymerase chain reaction (PCR).

As reported in "7.3 Taq DNA polymerase and its modifications" in: Pelt-Verkuil, Elizabeth van, Belkum, Alex van, Hays, John P. (2008) "Principles and Technical Aspects of PCR Amplification", Springer Netherlands (ISBN 978-90-481-7579-6), some manufacturers supply thermostable DNA polymerase or ready-made PCR master mixes that contain a reportedly inert red dye which does not interfere with either polymerase activity, purification of the amplified PCR product, sequencing or further downstream processing applications. Commercially available examples of these dye related products include REDAccuTaq®, REDTaq® (Sigma) and Red Hot® Taq DNA Polymerase (Thermo Fisher), and others. Such products serve as a tracking measure in that they allow the actual addition and mixing of polymerase or master mixes to be visually controlled. In addition, they facilitate visual tracking of the PCR amplification product on gel electrophoresis. In effect, these dyes act as a molecular weight marker corresponding to a 125 base pair DNA fragment. Another dye advertised as in inert colorant for the purpose of visibly indicating the presence or absence of a reagent in a vial is VisiBlue™ (TATAA Biocenter). WO2015/054396 discloses visible dye formulations as colorants for use with a qPCR master mix on real-time PCR instruments.

Reaction mixtures for PCR are examples for a biochemical or molecular biological reaction that after set-up is started by applying a temperature shift. More generally, concerning the processes of setting up biochemical or molecular biological reactions, the practitioner desires conditions under which the components of a reaction mixture maintain a tendency (i) to be chemically stable, (ii) to not react with each other and (iii) to not become dysfunctional with respect to the desired reaction to be performed later on. Well-known and frequently applied conditions to this end include low ambient temperatures such as temperatures in the range of 0° C. and 4° C. which provide such desired conditions for many biochemical reactants. In particular such low temperatures can be advantageous to inhibit biological activity of enzymes that originate from mesophilic organisms. However, many enzymes from thermostable organisms can be handled at room temperature as their catalytic activity unfolds at higher temperatures. Thus, a large number of preparatory processes of setting up biochemical or molecular biological reactions take place at a lower temperature than the temperature(s) at which the respective reaction proper is performed.

Technically, it is desired to have coloring agent as a marker component of a first liquid composition that would otherwise be indistinguishable from other liquid compositions the first composition could be confused with. Such a coloring agent would advantageously serve as a visual control in a manually performed process of combining different reagents in a reaction mixture. Ideally, such a visual control allows verification whether or not a particular reagent is already present in the mixture. Apart from visual control, a coloring agent is desired which is amenable to assessment by other optical means, particularly by means that can be automated.

In view of the fact that the purpose of the mixture is to allow a biochemical reaction to occur, the coloring agent is further desired to be inert with respect to the biochemical reaction; that is to say, the colorant should not inhibit or otherwise disadvantageously interfere with the biochemical reaction to be performed with the mixture.

In the particular case that during the course of the biochemical reaction any optical properties of the reaction mixture are subject to change, detection of such change is desired not to be disadvantageously affected by the colorant. This is a very specific requirement in case the biochemical reaction to be performed is real-time PCR that includes the step of monitoring fluorescent light emission during the thermocycling steps. A particular challenge in this regard is to find a coloring agent that does not quench fluorescence of one or more fluorescent dye(s) that might be present in the reaction mixture as part of a detection system indicating progress and/or result of the PCR process. Yet, another technical objective is given by the desire to combine visual control with automated control using a photometric readout that can be generated by a device such as, but not limited to, a thermocycler for real-time PCR.

With a more general focus on biochemical reactions that include a temperature shift the authors of the present disclosure took the approach of searching for thermolabile dyes that either have a color that is easily visible to the human eye, even at low concentrations, or dyes that are capable of exhibiting fluorescence. The search specifically focused on dyes that are thermolabile to minimize any influence on photometric detection that may be the case in the course of the processing of the reaction mixture the dye may be comprised in.

SUMMARY OF THE INVENTION

A first aspect related to all other aspects and embodiments as disclosed herein is an aqueous composition comprising a purified thermostable polypeptide with biological activity, and a purified thermolabile water-soluble substance which in a functional conformation at a permissive temperature absorbs light and/or exhibits fluorescence, wherein the maximal permissive temperature of the polypeptide is above the maximal permissive temperature of the substance. A second aspect related to all other aspects and embodiments as disclosed herein is a use of an aqueous composition according to the disclosure herein for indicating the presence of the thermostable polypeptide, the polypeptide being comprised in said composition. A third aspect related to all other aspects and embodiments as disclosed herein is a method of verifying the presence of a first component, and optionally the presence of a further component, in a process of combining a plurality of components to form a mixture, the method comprising the steps of (a) providing two or more components of the mixture as separate aqueous solutions, wherein one of the components comprises a purified thermostable polypeptide with biological activity; (b) selecting a first component and dyeing the first component with a first purified thermolabile water-soluble substance which in a functional conformation at a permissive temperature absorbs light and/or exhibits fluorescence, wherein the maximal permissive temperature of the polypeptide of step (a) is above the maximal permissive temperature of the first substance; (c) optionally selecting a further component and dyeing the further component with a further purified thermolabile water-soluble substance which in a functional conformation at a permissive temperature absorbs light and/or exhibits fluorescence, wherein the maximal permissive temperature of the polypeptide of step (a) is above the maximal permissive temperature of the further substance; (d) mixing the two or more components; (e) assessing a functional conformation of the first purified thermolabile water-soluble substance in the mixture obtained in step (d), thereby verifying the presence of the first component in the mixture; (f) optionally assessing a functional conformation of a further purified thermolabile water-soluble substance in the mixture obtained in step (d), thereby verifying the presence of the respective further component in the mixture; thereby verifying the presence of a first component, and optionally the presence of a further component, in the process of combining different reagents to form a mixture. A fourth aspect related to all other aspects and embodiments as disclosed herein is a method of identifying a processed status of a composition, wherein processing of the composition includes application of a temperature shift, the method comprising the steps of (a) providing an aqueous composition comprising a purified thermostable polypeptide with biological activity and a purified thermolabile water-soluble substance which in a functional conformation at a permissive temperature absorbs light and/or exhibits fluorescence, wherein the maximal permissive temperature of the polypeptide is above the maximal permissive temperature of the substance; (b) processing the composition of step (a) by applying a shift to a temperature above the maximal permissive temperature of the substance, wherein the conformation of the substance changes irreversibly thereby becoming dysfunctional; (c) assessing the functional conformation of the substance by optical means; thereby identifying the processed status of the composition. A fifth aspect related to all other aspects and embodiments as disclosed herein is a method of identifying a first unprocessed status and a second processed status of a composition, wherein processing of the composition includes application of a temperature shift, the method comprising the steps of (a) providing an aqueous composition comprising a purified thermostable polypeptide with biological activity and a purified thermolabile water-soluble substance which in a functional conformation at a permissive temperature absorbs light and/or exhibits fluorescence, wherein the maximal permissive temperature of the polypeptide is above the maximal permissive temperature of the substance; (b) keeping the composition of step (a) at a temperature below the maximal permissive temperature of the substance and without a temperature shift, whereby the conformation of the substance remains functional; (c) assessing the functional conformation of the substance by optical means; (d) processing the composition of step (a) by applying a shift to a temperature above the maximal permissive temperature of the substance, wherein the conformation of the substance changes irreversibly thereby becoming dysfunctional; (e) repeating step (c); thereby identifying the first unprocessed status and the second processed status of the composition. A sixth aspect related to all other aspects and embodiments as disclosed herein is a kit of parts comprising a purified thermostable polypeptide with biological activity and a purified thermolabile water-soluble substance which in a functional conformation at a permissive temperature absorbs light and/or exhibits fluorescence, wherein the maximal permissive temperature of the polypeptide is above the maximal permissive temperature of the substance.

DETAILED DESCRIPTION OF THE INVENTION

Certain terms are used with particular meaning, or are defined for the first time, in this report. For the purposes of the present disclosure, the terms used are defined by their art-accepted definitions, when such exist, except that when those definitions conflict or partially conflict with the definitions set forth below. In the event of a conflict in definition, the meaning of a term is first defined by any of the definitions set forth below.

The term "comprising" is used in the description of the invention and in the claims to mean "including, but not necessarily limited to".

The articles "a" and "an" are used herein to refer to one or to more than one (i.e. to at least one) of the grammatical object of the article. By way of example, "a compound" means one compound or more than one compound.

When designating a range of numerical values such as a concentration range, the range is indicated by a first value n1 and a second value n2. The lower boundary of the designated range is understood as being the value equal to or higher than the first value n1. The higher boundary of the designated range is understood as being the value equal to or lower than the second value n2. Thus, a value x in a designated range is given by n1≤x≤n2.

It is understood that the term "about" and the character "~" in combination with a numerical value n ("about n", "~n") indicates a value x in the interval given by the numerical value ±5% of the value, i.e. n−0.05*n≤x≤n+0.05*n. In case the term "about" or the character "~" in combination with a numerical value n describes a specific embodiment, the value of n is an even more specific embodiment, if not indicated otherwise.

The term "visible light" refers to the portion of the electromagnetic spectrum that is perceived by the human eye. A human eye is understood to respond to wavelengths from about 380 nm to about 750 nm. In terms of spectral colors a monochromatic wavelength in the range from about 380 nm to about 430 nm is perceived violet, blue in the range from about 430 nm to about 490 nm, green in the range from about 490 nm to about 570 nm, yellow in the range from about 570 nm to about 600 nm, orange in the range from about 600 nm to about 640 nm, and red in the range from about 640 nm to about 750 nm.

When light strikes an object, it can be absorbed, reflected, and/or scattered. When the surface absorbs all wavelengths of the incoming light equally, human perception indicates the object as black. The object is perceived white when the surface reflects all wavelengths equally. The term "color" denotes the visual perceptual property corresponding in humans to the categories called red, blue, yellow, etc. as mentioned above for monochromatic light of the visible spectrum. When some of the wavelengths present in white light are absorbed, then visual perception detects what is not absorbed as "colored" light. The color that is perceived is referred to as the complementary color of the color that was removed. For instance, if by way of absorption the red wavelengths are removed from white light, the perceived color is blue-green. Blue-green is complementary to red, and red is complementary to blue-green. Thus, color derives from the spectrum of light, i.e. the distribution of light power versus wavelength, interacting in the eye with the spectral sensitivities of the light receptors. A "colorant" is understood to be a first object with a color that can be mixed with colorless objects. Some objects, particularly colored liquids can not only reflect light, but in specific embodiments also transmit light or emit light themselves, which also contribute to the color. A colorless transparent liquid can be colored by adding a dye that is soluble in the liquid as a colorant. A "dye" is a compound capable of absorbing light at one or more wavelengths. In the context of the present disclosure, a dye is a water-soluble substance which in a functional conformation at a permissive temperature absorbs light and/or exhibits fluorescence. One non-limiting specific embodiment of a dye that is well known to the art is a non-fluorescent dye. A further non-limiting specific embodiment of a dye that is well known to the art is a "fluorescent dye" which is characterized by the property of re-emitting light upon excitation, i.e. "fluorescence".

In the context of the present disclosure a material (such as, but not limited to, a polypeptide with biological activity or a substance which absorbs light and/or exhibits fluorescence) is understood to be "thermolabile" if the material is functionally incapacitated including destroyed, denatured, decomposed, rendered dysfunctional, or otherwise inactivated, by way of change in its chemical and/or physical structure, as an irreversible response to exposure to heat above a permissive temperature. For each material considered, the "permissive temperature" defines the temperature up to which the material is functional and capable of exhibiting characteristic features which above the permissive temperature are functionally incapacitated in an irreversible way. The capability of exhibiting characteristic features is understood to include reversible inactivation; thus, above a certain temperature the material may cease to be functional but returns to being functional once the temperature is lowered again. The term "permissive temperature" therefore encompasses thermal conditions under which reversible inactivation is the case. For each material considered, the temperature above which irreversible changes occur is referred to as "maximal permissive temperature". The terms "thermostability" and "thermostable" denote the quality of a first material relative to a second material to resist irreversible change in its chemical and/or physical structure at a temperature at which a second material is thermolabile.

One aspect related to all other aspects and embodiments as disclosed herein is an aqueous composition comprising a (one or more) purified thermostable polypeptide with biological activity, and a (one or more) purified thermolabile water-soluble substance which in a functional conformation at a permissive temperature absorbs light and/or exhibits fluorescence, wherein the maximal permissive temperature of the polypeptide is above the maximal permissive temperature of the substance.

A further embodiment of all aspects as disclosed herein is the use of an aqueous composition as disclosed herein, for indicating the presence of the thermostable polypeptide, the polypeptide being comprised in said composition. Yet, a specific embodiment of all aspects as disclosed herein is the use of an aqueous composition as disclosed herein, for additionally indicating the absence of exposure of the composition to a temperature above the maximal permissive temperature of the thermolabile water-soluble substance, the substance being comprised in said composition, wherein the substance in a functional conformation at a permissive temperature absorbs light and/or exhibits fluorescence, and wherein the maximal permissive temperature of the polypeptide is above the maximal permissive temperature of the substance. Yet, another specific embodiment of all aspects as disclosed herein is the use of an aqueous composition as disclosed herein, for additionally an exposure of the composition to a temperature above the maximal permissive temperature of the thermolabile water-soluble substance, the substance being comprised in said composition, wherein the substance in a functional conformation at a permissive temperature absorbs light and/or exhibits fluorescence, and wherein the maximal permissive temperature of the polypeptide is above the maximal permissive temperature of the substance.

Importantly, the maximal permissive temperature of the polypeptide is above the maximal permissive temperature of the substance. In a specific embodiment of all aspects as disclosed herein at a permissive temperature for the polypeptide, the polypeptide has biological activity, or biological activity of the polypeptide is reversibly blocked. In line with the above-described understanding of "permissive temperature", the physico-chemical state of the polypeptide is compatible with displaying or re-acquiring a conformation that allows function, biological function in this regard. Thus, in a specific embodiment of all aspects as disclosed herein up to the maximal permissive temperature of the polypeptide, the polypeptide has biological activity, or biological activity of the polypeptide is reversibly blocked. So in a more specific embodiment of all aspects as disclosed herein above the maximal permissive temperature of the polypeptide, the polypeptide has no biological activity and biological activity of the polypeptide is irreversibly blocked.

As already mentioned above, in the compositions as disclosed herein the maximal permissive temperature of the substance is lower than the maximal permissive temperature of the polypeptide. The functional conformation is dependent on a permissive temperature. Only in a functional conformation the substance absorbs light and/or exhibits fluorescence. In yet another specific embodiment of all aspects as disclosed herein at a permissive temperature for the substance, the substance is in a functional conformation and absorbs light and/or exhibits fluorescence, with the proviso that the substance is not exposed to a temperature above the maximal permissive temperature of the substance. Thus, in a further specific embodiment of all aspects as disclosed herein up to the maximal permissive temperature of the substance, the substance is in a functional conformation and absorbs light or exhibits fluorescence, again with the proviso that the substance is not exposed to a temperature above the maximal permissive temperature of the substance. So in a more specific embodiment of all aspects as disclosed herein above the maximal permissive temperature of the substance the conformation of the substance changes irreversibly thereby becoming dysfunctional.

The range of permissive temperatures of the polypeptide with biological function advantageously overlaps with the range of permissive temperatures of the water-soluble substance which in a functional conformation at a permissive temperature absorbs light and/or exhibits fluorescence. Thus, a further aspect related to all other aspects and embodiments as disclosed herein is an aqueous composition comprising a purified thermostable polypeptide with biological activity, and a purified thermolabile water-soluble substance which in a functional conformation at a permissive temperature absorbs light and/or exhibits fluorescence, wherein the maximal permissive temperature of the polypeptide is above the maximal permissive temperature of the substance, wherein the maximal permissive temperature of the substance is a permissive temperature for the polypeptide.

Inactivation of the substance by non-permissive temperatures may follow different kinetics. Upon applying a temperature shift reaching above the maximal permissive temperature of the substance, the substance starts to lose its functional conformation, thereby losing the capability of absorbing light or exhibiting fluorescence. Such loss of function can be fast or slow, the latter case causing a gradual change. On a molecular level, there will be individual molecules of the substance, the largest part of which will be irreversibly dysfunctional; at the same time, depending on the time interval of the incubation with a non-permissive high temperature and on the temperature itself, there may be a small group of residual molecules of the substance which remain functional, at least for a short time. For example, a very short time interval of incubation at a non-permissive temperature that is just slightly higher that the maximal permissive temperature of the substance may leave a certain portion of the substance functional. Advantageously, and in a further specific embodiment of all aspects as disclosed herein the thermolabile substance is chosen such that at a temperature above the maximal permissive temperature of the substance 75% or more of the substance's capability of absorbing light and/or exhibiting fluorescence in the composition is irreversibly blocked. If in a case of gradual inactivation after the short time interval the temperature is lowered again to a temperature in the range of permissive temperatures for the substance, residual substance with a functional conformation will still be capable of absorbing light or exhibiting fluorescence. Therefore, in a further specific embodiment of all aspects as disclosed herein, relative to a first temperature that is permissive for both the polypeptide and the substance, at a second temperature which is higher than the first temperature and above the maximal permissive temperature of the substance (a) 50% or more of the biological activity of the polypeptide is present or blocked reversibly, and (b) 75% or more of the substance has a dysfunctional conformation. More specifically, at the second temperature at least an amount of the biological activity of the polypeptide is present or blocked reversibly, the amount being selected from the group consisting of 55%, 60%, 65%, 70%, 75%, 80%, 85%, 90%, and 95%. Even more specifically, at the second temperature at least an amount of the substance has a dysfunctional conformation, the amount being selected from the group consisting of 80%, 85%, 90%, 95%, and 100%. Thus, at the second temperature at least an amount of the substance's capability of absorbing light and/or exhibiting fluorescence in the composition is irreversibly blocked, the amount being selected from the group consisting of 75%, 80%, 85%, 90%, 95%, and 100%.

The polypeptide with biological activity is chosen to be thermostable within the range of permissive temperatures of the substance. Importantly, the maximal permissive temperature of the polypeptide with biological activity is higher than the maximal permissive temperature of the substance. In a very advantageous specific embodiment of all aspects as disclosed herein the polypeptide with biological activity originates from a thermophilic organism. A thermophile is an extremophile organism which exists at relatively high temperatures, between about 40° C. and about 120° C. Thermophiles are discriminated from mesophiles. Many thermophiles are archaea, but also thermophilic eubacteria are known. Thermophiles are typically found in various geothermally heated regions of the Earth, such as hot springs and deep sea hydrothermal vents, as well as in decaying plant matter, such as peat bogs and compost. Unlike other types of bacteria, thermophiles can survive at much hotter temperatures, whereas other bacteria would be damaged and sometimes killed if exposed to the same temperatures. As a prerequisite for their survival, thermophiles contain enzymes that can endure and even function at high temperatures. Some of these enzymes are used in isolated form in molecular biology, for example, heat-stable DNA polymerases for PCR. In a specific embodiment of all aspects as disclosed herein the polypeptide with biological activity is an enzyme, more specifically an enzyme which has the activity of a template-dependent RNA or DNA polymerase.

Considering any biological activity with respect to target molecules, in further a specific embodiment of all aspects as disclosed herein any composition as disclosed further contains a molecule which is a substrate of the enzyme or a co-substrate for the enzyme. In biochemistry and molecular biology more specifically, the substrate is a molecule upon which an enzyme acts. Enzymes catalyze chemical reactions involving the substrate(s). In the case of a single substrate, the substrate bonds with the enzyme active site, and an enzyme-substrate complex is formed. The substrate is transformed into one or more products, which are then released from the active site. The active site is then free to accept another substrate molecule. In the case of more than one substrate, these may bind in a particular order to the active site, before reacting together to produce products. In this regard, a co-substrate (also sometimes called co-enzyme) may be present in some enzyme-catalyzed reactions. A co-substrate does not possess catalytic activity itself but is ancillary to the enzyme to exhibit its catalytic activity. The co-substrate typically acts as a helper substance in that it provides the transfer site for biochemical reactions catalyzed by an enzyme, and in that it is reacted by the enzyme together with the substrate.

In a specific embodiment a substrate contained in a composition as disclosed in all aspects and embodiments herein is a nucleic acid, more specifically a nucleic acid or functional equivalent thereof capable of being processed by a template-dependent RNA or DNA polymerase, even more specifically a DNA or RNA molecule, optionally comprising one or more detectable labels, even more specifically double-stranded, single-stranded or in mixed conformations thereof. Further comprised in this regard are DNA or RNA molecules that contain a detectable label such as, but not limited to, a biotin residue, a digoxigenin residue or a fluorophore. Further comprised in this regard are DNA or RNA molecules that contain a nucleoside analogue such as, but not limited to, a dideoxynucleoside, and a nucleoside comprising a detectable label such as, but not limited to digoxigenin residue or a fluorophore. Further, in a more specific embodiment a substrate is a nucleoside triphosphate, a deoxyribonucleoside triphosphate, or a functional equivalent thereof. In this regard a functional equivalent thereof is capable of being processed by the enzyme, i.e. the template-dependent RNA or DNA polymerase. Such functional equivalents include nucleoside triphosphates or deoxyribonucleoside triphosphates comprising a detectable label such as, but not limited to, a biotin residue or a fluorophore.

In all aspects and embodiments as disclosed herein, the purified thermolabile water-soluble substance which in a functional conformation at a permissive temperature absorbs light, specifically visible light, more specifically light in a range of wavelengths from 380 nm to 750 nm, even more specifically light in a range of wavelengths from 500 nm to 650 nm. It has been found that an advantageous thermolabile water-soluble substance comprises a polypeptide component and optionally a chromophore. Thus, with great advantage and in a specific embodiment of all aspects as disclosed herein the substance comprises a bacteriorhodopsin or a functional variant or derivative thereof.

Thermostable/thermolabile The subject thermostable polypeptide (e.g. enzyme) and soluble thermolabile dye, i.e. in the embodiment of the purified thermolabile water-soluble substance which in a functional conformation at a permissive temperature absorbs light, are characterized by different specific properties relating to their respective functional states at different temperatures. Essentially, the maximal permissive temperature of the polypeptide is above the maximal permissive temperature of the substance. The thermolabile dye in its undenatured form, i.e. in its functional conformation is capable of absorbing visible light. The undenatured form is present at a permissive temperature which allows the dye to exist a chemical and/or physical state that is compatible with its light absorbing property. Once the temperature is raised above the maximum permissive temperature, the dye irreversibly loses its ability to absorb visible light. The threshold temperature of the thermolabile dye in the aqueous composition according to the present disclosure is chosen such that it is within a functional temperature range of the thermostable polypeptide (e.g. thermostable enzyme) in the aqueous composition. In a specific embodiment, the thermolabile dye irreversibly loses its ability to absorb visible light in a temperature range where in the composition the thermostable enzyme is either still active or just reversibly inhibited, but not irreversibly denatured in a substantial relative amount.

In specific embodiments of all aspects as disclosed in this report, the thermolabile dye is a thermolabile bacteriorhodopsin. The generic term "bacteriorhodopsin" (=BR; reviewed by Trivedi S. Recent Patents on DNA & Gene sequences 5 (2011) 35-40) refers to an integral membrane protein found in the purple membrane mainly in Halobacteria (Archaea). This protein purified from bacterial biomass absorbs green light (wavelength 500-650 nm, with an absorption maximum at about 568 nm) and converts it into an electrochemical gradient which is used in the bacterium for ATP production. The cofactor retinal that is covalently bound in the binding site of BR has been replaced by a large number of different chemical structures, and the modified properties attained therewith include color and photochemical behavior. Depending on the number of conjugated double bonds in a functional retinal analogue, material of almost any absorption characteristic in the visible and near-infrared can be created (Oesterheld D. et al. Quarterly Reviews of Biophysics 24 (1991) 425-478). Further, the polypeptide moiety of BR has been subject of molecular design, e.g. to change certain properties of the surface of the BR molecule (Mitra K. et al. Protein Engineering 15 (2002) 485-492). Concerning the different physical and chemical conformations that have been described for bacteriorhodopsin of functional variants and equivalents thereof, the understanding according to the present disclosure is that a functional conformation corresponds to a thermolabile conformation capable of absorbing light at a permissive temperature.

The three-dimensional tertiary structure of BR resembles that of vertebrate rhodopsins. BR has a typical retinylidene protein structure where there are seven transmembrane alpha helices and one retinal is buried within. The chromophore is covalently linked to a Lysine residue through a Schiff base link. Functions of rhodopsin and bacteriorhodopsin are different and there is little homology in their amino acid sequences. BR is reported to be stable in the absence of salts, resistant to digestion by most proteases, retains photochemical properties over long periods, functions between 0° C. and 45° C. in the pH range 1-11 and tolerates temperatures of over 80° C. in water and up to 140° C. when dry (Trivedi S., supra). Methods to isolate BR are well known to the art and exemplified herein in a non-limiting way by Example 1. Other methods were reported, e.g. in Seyedkarimi, M.-S. et al. Extremophiles 19 (2015) 1021-1028. The specific embodiments referring to purified bacteriorhodopsin with respect to all aspects as disclosed herein also by the same token encompass solubilized membrane vesicles with bacteriorhodopsin isolated from cultivated biomass of a member of the Euryarchaeota, e.g. isolated from residual biomass as purple membrane vesicles containing bacteriorhodopsin. For the purpose of the present disclosure, preparation of bacteriorhodopsin and/or purple membrane vesicles do not have to function as proton translocation systems but are technically sufficient as long as such material in a functional conformation at a permissive temperature absorbs light, and as long as such material is thermolabile as described here in general terms for the substance which in a functional conformation at a permissive temperature absorbs light, wherein the maximal permissive temperature of the polypeptide (e.g. the thermostable enzyme) is above the maximal permissive temperature of the substance.

In yet more specific embodiments of all aspects as disclosed in this report, the thermolabile dye, i.e. the thermolabile water-soluble substance which in a functional conformation at a permissive temperature absorbs light is bacteriorhodopsin from *Halobacterium salinarum*, also known as *Halobacterium halobium*. This particular thermolabile BR has been described in the literature to some extent, as the first example of a bacteriorhodopsin. By way of differential scanning calorimetry Jackson, M B & Sturtevant J M Biochemistry 17 (1978) 911-915 reported for purple membranes isolated from *Halobacterium halobium* two transition states, one at about 80° C. (also referred to as pretransition in the literature) and the other (the main transition) at about 95° C.-100° C. No transition was seen from 0° C. to 75° C. In a later study, Cladera J et al. (Eur. J. Biochem. 207 (1992) 581-585) found that the main thermal transition in the purple membrane is due to a cooperative conformational change involving the disruption of the network of electrostatic and hydrogen-bonding interactions. The thermal transition of BR was described as being accompanied by decoloration due to the hydrolysis of the retinal Schiff base being the covalent connection to the binding site in the BR polypeptide. In fact, thermal bleaching of BR is the consequence of irreversible denaturation of the BR polypeptide, cleavage of the covalent bond to the cofactor retinal, and thereby loss of the color-mediating cofactor.

On the one hand, native, i.e. non-denatured BR from archaebacterial purple membranes can be used as a water-soluble dye capable of absorbing visible light. With regards to a reaction mixture with a thermostable nucleotide polymerase enzyme it was surprisingly found that BR behaves as an inert ingredient relative to nucleoside/deoxynucleoside triphosphates and DNA or RNA polymerase enzymes. Also, any products from light-induced bleaching of BR, i.e. the incapacitated and concerning light absorption dysfunctional form of BR, particularly bacteriorhodopsin from *Halobacterium salinarum*, does not interfere with DNA or RNA polymerase enzymes, and also not with their interactions with nucleoside/deoxynucleoside triphosphates; further, there is no detectable inhibitive action with respect to the enzyme/substrate interaction with a template nucleic acid.

In all aspects and embodiments as disclosed herein, the purified thermolabile water-soluble substance which in a functional conformation at a permissive temperature exhibits fluorescence. In a specific embodiment of all aspects as disclosed herein, the fluorescence of the substance has an emission wavelength in the range of 350 nm to 700 nm. In yet another a specific embodiment of all aspects as disclosed herein, fluorescent light is emitted upon excitation with light having a wavelength in the range of 300 nm to 650 nm. It has been found that an advantageous thermolabile fluorescent substance comprises a polypeptide component and optionally a chromophore. Thus, with great advantage and in a specific embodiment of all aspects as disclosed herein the substance comprises a fluorescent protein or a functional variant or derivative thereof.

Thermostable/thermolabile The subject thermostable polypeptide (e.g. enzyme) and fluorescent soluble thermolabile substance (e.g. fluorescent protein), i.e. in the embodiment of the purified thermolabile water-soluble substance which in a functional conformation at a permissive temperature exhibits fluorescence, are characterized by different specific properties relating to their respective functional states at different temperatures. Essentially, the maximal permissive temperature of the polypeptide is above the maximal permissive temperature of the substance. The thermolabile fluorescent dye in its undenatured form, i.e. in its functional conformation is capable of absorbing light at a specific excitation wavelength and exhibiting fluorescence. The undenatured form is present at a permissive temperature which allows the fluorescent dye to exist a chemical and/or physical state that is compatible with its light absorbing and fluorescing properties. Once the temperature is raised above the maximum permissive temperature, the dye irreversibly loses its ability to absorb light and/or exhibit fluorescence. The threshold temperature of the thermolabile fluorescent dye in the aqueous composition according to the present disclosure is chosen such that it is within a functional temperature range of the thermostable polypeptide (e.g. thermostable enzyme) in the aqueous composition. In a specific embodiment, the thermolabile fluorescent dye irreversibly loses its ability to absorb light and/or exhibit fluorescence in a temperature range where in the composition the thermostable enzyme is either still active or just reversibly inhibited, but not irreversibly denatured in a substantial relative amount.

In yet more specific embodiments of all aspects as disclosed in this report, the thermolabile fluorescent dye, i.e. the thermolabile water-soluble substance which in a functional conformation at a permissive temperature exhibits fluorescence is a fluorescent protein selected from the group consisting of Green Fluorescent Protein, Enhanced Green Fluorescent Protein, Yellow Fluorescent Protein, Blue Fluorescent Protein, Cyan Fluorescent Protein, Red Fluorescent Protein/R-Phycoerythrin, and Red Fluorescent Protein/dsRed.

The green fluorescent protein (GFP) is a protein composed of 238 amino acid residues (26.9 kDa) that exhibits bright green fluorescence when exposed to light in the blue to ultraviolet range. Although many other marine organisms have similar green fluorescent proteins, GFP traditionally refers to the protein first isolated from the jellyfish *Aequorea victoria*. The GFP from *A. victoria* has a major excitation peak at a wavelength of 395 nm and a minor one at 475 nm. Its emission peak is at 509 nm, which is in the lower green portion of the visible spectrum. The GFP from the sea pansy (*Renilla reniformis*) has a single major excitation peak at 498 nm. In cell and molecular biology, the GFP gene is frequently used as a reporter of expression. In modified forms it has been used to make biosensors, and many animals have been created that express GFP as a proof-of-concept that a gene can be expressed throughout a given organism. The GFP gene can be introduced into organisms and maintained in their genome through breeding, injection with a viral vector, or cell transformation. Enhanced Green Fluorescent Protein (EGFP) is recombinantly expressed and purified from transformed *E. coli*. The recombinant EGFP (Gene Bank Accession no. U57607) is a 32.7 kDa monomer with 293 amino acids, including an optional His-tag. The excitation and emmission spectra for the recombinant EGFP is identical to GFP purified from *Aequorea victoria*, with excitation/emission wavelengths are 488 and 507 nm, respectively. EGFP is commercially available, e.g. from BioVision, Inc., Milpitas, Calif. (USA), catalog #4999-100. Yellow Fluorescent Protein (YFP) is recombinantly expressed and purified from transformed *E. coli*. The protein is a 26.4 kDa monomer with 238 amino acids, excitation/emission wavelengths are 525 and 538 nm. YFP is commercially available, e.g. from BioVision, catalog #4998-100. Blue Fluorescent Protein (BFP) is recombinantly expressed and purified from transformed *E. coli*. The protein is a 29 kDa monomer with 259 amino acids, including an optional His-tag, isoelectric point: 6.17. Excitation wavelengths are 308 nm to 383 nm; Emission wavelengths are 440 to 447 nm. BFP is commercially available, e.g. from BioVision, catalog #4994-100. Cyan Fluorescent Protein (CFP) is recombinantly expressed and purified from transformed *E. coli*. The protein is a 31.3 kDa monomer with 284 amino acids including an optional His-tag, excitation/emission wavelengths are 458 nm and 480 nm, respectively. CFP is commercially available, e.g. from BioVision, catalog #5986-100. Red Fluorescent Protein/dsRed is recombinantly expressed and purified from transformed *E. coli*. The protein is a 27.6 kDa monomers containing an optional His-tag, excitation/emission wavelengths are 557 and 585 nm respectively. Red Fluorescent Protein/dsRed is commercially available, e.g. from BioVision, catalog #4997-100. Red Fluorescent Protein/R-Phycoerythrin (R-PE) is an intensely bright phycobiliprotein isolated from red algae that exhibits extremely bright red-orange fluorescence with high quantum yields. R-PE consists of a, b and g subunits and is present as (ab) 6g. R-PE and the closely related B-PE (B-phycoerythrin) are the most intensely fluorescent phycobiliproteins having orange fluorescence. R-PE is a large molecule frequently used for fluorescence-based detection, including in conjugates. Red Fluorescent Protein/R-Phycoerythrin is commercially available, e.g. from BioVision, catalog #6005-1.

In another specific embodiment of all aspects as disclosed herein there is reported an aqueous composition comprising a purified thermostable polypeptide with biological activity, and a purified thermolabile water-soluble substance which in a functional conformation at a permissive temperature absorbs light and/or exhibits fluorescence, wherein the maximal permissive temperature of the polypeptide is above the maximal permissive temperature of the substance, wherein the composition further comprises a plurality of different purified thermolabile water-soluble substances, and wherein the maximal permissive temperature of the polypeptide is above the maximal permissive temperature of each of the substances. In a more specific embodiment of all aspects as disclosed herein at least a first substance in a functional conformation at a permissive temperature absorbs light, and at least a second substance in a functional conformation at a permissive temperature exhibits fluorescence. Very advantageous and of high practical use in this regard is an aqueous composition comprising a (one or more) purified thermostable template-dependent enzyme with DNA and/or RNA polymerase activity, a thermolabile fluorescent protein and a thermolabile bacteriorhodopsin as dyes in the composition. In such a specific embodiment, at a permissive temperature for the enzyme, the enzyme has biological activity, or biological activity of the enzyme is blocked reversibly. The range of the permissive temperatures of the enzyme (or the plurality of thermostable enzymes that may be present in the composition) extends above the maximal permissive temperature of both the fluorescent protein and the maximal permissive temperature of the bacteriorhodopsin. Thus, relative to a first temperature that is permissive for both the enzyme(s) and the dyes, at a second temperature which is higher than the first temperature and above the maximal permissive temperature of the dyes (a) 50% or more of the biological activity of the enzyme(s) is present or blocked reversibly, and (b) 75% or more of each of the dyes has a dysfunctional conformation. More specifically, at the second temperature at least an amount of each of the dyes has a dysfunctional conformation, the amount being selected from the group consisting of 80%, 85%, 90%, 95%, and 100%.

In yet a further specific embodiment of all aspects as disclosed herein the aqueous composition is housed in one or more reaction vessel(s), specifically a plurality of reaction vessels in the form of a microwell plate. In a more specific embodiment of all aspects as disclosed herein the aqueous composition comprises one or more thermostable enzymes with DNA and/or RNA polymerase activity, and one or more vessels comprising the aqueous composition is/are placed in a real-time PCR instrument.

Biochemical or molecular biological reactions which are started with a temperature shift include but are not limited to the polymerase chain reaction (PCR). PCR is a procedure that produces multiple copies of a segment of DNA through cycles of: (1) denaturation (heat-induced separation of double-stranded DNA into single strands); (2) annealing (binding of specific primers on either end of the target segment); and (3) elongation (extension of the primer sequences over the target segment by incorporation of nucleoside triphosphates (dNTPs) with DNA polymerase). The amplified product (PCR product), doubled each cycle for a fixed number of cycles (e.g. 30 or more), can then be subjected to further testing. Since the denaturation step (1) requires a temperature shift, PCR is typically performed using thermostable DNA polymerases which are derived from thermophilic organisms such as but not limited to *Thermus aquaticus, Pyrococcus furiosus* and *Thermococcus litoralis*.

While an endpoint assay measures the amount of accumulated PCR product at the end of the last PCR cycle, real-time polymerase chain reaction (real-time PCR) monitors the amplification of a PCR product during the progress of the PCR as it occurs (i.e., in real time). Data is therefore collected throughout the PCR process (during the fixed number of cycles), rather than at the end of the PCR, following the last cycle, i.e. the endpoint. In real-time PCR, reactions are characterized by the point in time during cycling when amplification of a PCR product is first detected rather than the amount of PCR product accumulated after a fixed number of cycles. The higher the starting copy number of the nucleic acid target, the sooner a significant increase of an indicator of amplification of the PCR product is observed.

There are a number of different technical possibilities to provide the effect of an indicator of amplification of the PCR product in real-time PCR. Typically and well-known to the art, the indicator is a light signal based on fluorescence. The fluorescence that is monitored during the real-time PCR process can be detected using a nonspecific detection approach independent of the target sequence, e.g. through fluorescent dyes that have special fluorescent properties when bound to dsDNA (e.g. SYBR® Green I or other intercalating dyes), or by making use of sequence-specific fluorescent oligonucleotide probes; i.e. a sequence-specific approach (such as TaqMan® hydrolysis probes, Molecular Beacons).

There is a number of different commercially available instruments to perform real-time PCR, i.e. real-time PCR thermal cyclers. The essential parts of a real-time PCR thermal cycler are a thermal system to perform temperature cycling, an optical system to emit light necessary for activation of the fluorophore(s) combined with a system to capture the generated fluorescence, and software to control the instrument operation, and collect and analyze the data generated.

The optical system in a real-time PCR thermal cycler comprises two main parts: a light source for excitation of one or more fluorescent dye(s), and a detector to monitor emitted fluorescence. The excitation light source can be classified into broad or narrow spectrum. In broad spectrum, light source filters can be used to narrow the light down to a suitable wavelength range for a particular fluorophore. Other instruments employ narrow spectrum light sources including laser and light-emitting diodes. The detector part of the optical system records the light emitted from the reporter fluorophores. Most systems use photo-multiplier tubes (PMTs), photodiodes or charge-coupled device (CCS) cameras. CCD cameras can record all wells simultaneously, leading to a more robust mechanical design, whereas both photodiodes and PMTs record one point at a time. Some instruments utilize multiple photodiodes or PMTs which reduces the number of moving parts. The number of channels detected is typically between one and six.

Each channel in an instrument for real-time PCR is characterized by a defined wavelength interval of the light spectrum and has its corresponding light source, filter set and detector. The wavelength interval of a detected channel is selected to match the light emission of a corresponding fluorescent dye. That is to say, in a multi-channel instrument the fluorescence coming from a particular dye is ideally detected in a single channel, only, and not in another channel. Particularly multiplex PCR methods, e.g. based on TaqMan® probes as well as FRET (fluorescence resonance energy transfer)-based systems are typically performed with fluorescent dyes such as, but not limited to, FITC, JOEL, ROX, HEX, TAMRA, Texas Red, Quasar 705 and Cy5, and used in instruments with multiple optical channels.

Many instruments for performing real-time PCR are optimized for specific dyes. Some platforms are delivered pre-calibrated for certain dyes, and thus show optimal performance with these particular dyes, although dyes with similar excitation and emission wavelengths can be used. For some platforms, it is necessary to run calibrations before using the instruments.

Typically, PCR and particularly real-time PCR is performed in one or more vials (tubes). Vials can be provided as a plurality and grouped in an array, also known as a microwell or multiwell plate. There are different formats for multiple reaction vials used with cycler platforms. Several of the available instruments use a standard 96-well block format. Further, there are systems that offer the possibility to use 384- and/or 1536-well blocks, sometimes within the same system as for the 96-well block format. Additionally, platforms with up to 48-wells are being commercialized, offering an intermediate solution between handling single tubes (vials) and using 96-well plates.

Before a reaction is started, reagents comprising the necessary components of a single reaction have to be combined in each vial. The reagents are typically provided as aqueous solutions which may contain template DNA, oligonucleotide primers, DNA polymerase enzyme(s), nucleoside triphosphates (or functional analogues thereof), labeled oligo nucleotides, intercalation dyes, buffer(s), salt (s), and other compounds. Frequently, certain ingredients are combined ("pre-mixed" or "premixed") prior to being added to a PCR reaction mixture. An example therefor is a so-called "master mix". A PCR "master mix" provides a plurality of ingredients necessary for performing PCR in a premixed and optimized format that streamlines and simplifies the PCR workflow. Typical exemplary master mixes which are commercially available contain a DNA polymerase, salts, magnesium or other bivalent ions, dNTPs, and optimized reaction buffer. In order to form a complete reaction mixture suitable for performing PCR only template DNA and primers need to be added.

The present disclosure reports an aqueous composition comprising a thermostable polypeptide such as, but not limited to, an enzyme and a soluble thermolabile dye, wherein the thermolabile dye in its functional, undenatured form is capable of absorbing visible light. The indicator dye as disclosed in here is advantageously used as a visual control in a process, specifically in a manually performed process, of combining different reagents in a reaction mixture that is to be exposed to a temperature shift. Before the temperature shift is applied, the thermolabile indicator dye being part of a reagent indicates the presence of the reagent visibly to the human eye. Thus, when combining two or more different colorless aqueous solutions to form a reaction mixture, the presence or absence of one component, namely the one containing the indicator dye, can be visibly verified. Thus, the present disclosure provides a method of verifying the presence of a first component in a process of combining different reagents to form a reaction mixture, the method comprising the steps of (a) providing two or more components of the reaction mixture as separate aqueous solutions, (b) mixing a first component with a first dye, (c) mixing a second component with the dyed first component and detecting the first dye in the mixture, thereby verifying the presence of the first component in the mixture. Such a method is particularly useful when large numbers of reaction mixtures are to be prepared manually. In an exemplified case there is a number of reaction vessels corresponding to the number of desired reaction mixtures. In a first step of liquid handling, specifically manual pipetting, the aqueous solution of the component A is added into each vessel. At this stage visual or other control can differentiate without much difficulty between an unprocessed empty vessel and a vessel that already contains the aliquot of the component A. In a subsequent step of liquid handling, the component B is added. Particularly in cases where the added volume of the components A and B is not markedly different from the volume of component A alone, particularly visual control to monitor any errors of manual liquid handling is a challenge and may lead to a certain number of reaction vessels that eventually may lack component B. That is to say, a pipetting error leading to lack of component B in a vessel may not be recognized. The same kind of error is possible in cases where the volumes of the two components are so small that particularly the human eye cannot clearly distinguish between the added volume of the first and the second component on the one hand, and on the other hand the volume of the first component alone. Such a source of error can be avoided by adding a dye to one component, specifically to the component the presence of which is required to be recognized visually or by other means that are based on detection of the dye.

In case there is a further essential component to be added to the mixture, a further (second) dye used as an ingredient of the further component can provide technical advantage, for the purpose of verifying the presence of the further component in the mixture. However, for this purpose the further dye requires to be capable of being identified in the presence of the first dye. Accordingly, the present disclosure provides a method of verifying the presence of a first and a second component in a process of combining different reagents to form a reaction mixture, the method comprising the steps of (a) providing three or more components of the reaction mixture as separate aqueous solutions; (b) mixing a first component with a first dye and mixing a second component with a second dye; (c) mixing a third component with the dyed first component and optionally detecting the first dye in the mixture, thereby verifying the presence of the first component in the mixture; (d) mixing the dyed second component with the mixture of step (c) and optionally detecting the second dye in the mixture, thereby verifying the presence of the second component in the mixture; (e) unless already performed in steps (c) and/or (d) detecting the first and/or the second dye in the mixture of step (d), thereby verifying the presence of the first and the second component. Importantly, the dyes must be selected such that detection of each dye can occur independently of the other. Thus, the first dye must not completely mask the second dye, and vice versa.

The different components referred to are reagents provided as aqueous solutions which are combined to form a reaction mixture. That is to say, the different reagents comprise reaction partners which can take part in a reaction when combined in a mixture with each other, under conditions allowing the reaction to occur.

As mentioned above, an aspect related to all other aspects and embodiments as disclosed herein is the use of an aqueous composition according to the disclosure herein for indicating the presence of the thermostable polypeptide, the polypeptide being comprised in said composition. Yet, a further aspect related to all other aspects and embodiments as disclosed herein is a method of verifying the presence of a first component, and optionally the presence of a further component, in a process of combining a plurality of components to form a mixture, the method comprising the steps of (a) providing two or more components of the mixture as separate aqueous solutions, wherein one of the components comprises a purified thermostable polypeptide with biological activity; (b) selecting a first component and dyeing the first component with a first purified thermolabile water-soluble substance which in a functional conformation at a permissive temperature absorbs light and/or exhibits fluorescence, wherein the maximal permissive temperature of the polypeptide of step (a) is above the maximal permissive temperature of the first substance; (c) optionally selecting a further component and dyeing the further component with a further purified thermolabile water-soluble substance which in a functional conformation at a permissive temperature absorbs light and/or exhibits fluorescence, wherein the maximal permissive temperature of the polypeptide of step (a) is above the maximal permissive temperature of the further substance; (d) mixing the two or more components; (e) assessing a functional conformation of the first purified thermolabile water-soluble substance in the mixture obtained in step (d), thereby verifying the presence of the first component in the mixture; (f) optionally assessing a functional conformation of a further purified thermolabile water-soluble substance in the mixture obtained in step (d), thereby verifying the presence of the respective further component in the mixture; thereby verifying the presence of a first component, and optionally the presence of a further component, in the process of combining different reagents to form a mixture.

In a specific embodiment, the mixture of step (d) comprises the purified thermostable polypeptide with biological activity of step (a), the substance of step (b), and optionally a further substance of step (c). In a further specific embodiment, the mixture of step (d) is an aqueous solution. More specifically, the thermostable polypeptide with biological activity is a template-dependent enzyme with DNA and/or RNA polymerase activity. In yet another specific embodiment, the steps (a) through (f) are performed at a temperature below the maximal permissive temperature of the substance and without a temperature shift, whereby the conformation(s) of the first substance and an optional further substance remain(s) functional. In yet a further specific embodiment, first substance is a thermolabile fluorescent protein and a second substance is a thermolabile bacteriorhodopsin. Yet, in a further specific embodiment any of the steps (e) and (f) comprise assessment by any of visual inspection, colorimetric measurement, and fluorescence measurement. In a further specific embodiment, the method further comprises an additional step (g) of processing the composition of step (d) by applying a temperature above the maximal permissive temperature of the substance, wherein the conformation of the first substance and an optional further substance change(s) irreversibly thereby becoming dysfunctional. In yet a further specific embodiment, the method further comprises an additional step (h) of optical assessment, specifically assessment by any of visual inspection, colorimetric measurement, and fluorescence measurement.

Figure 1:
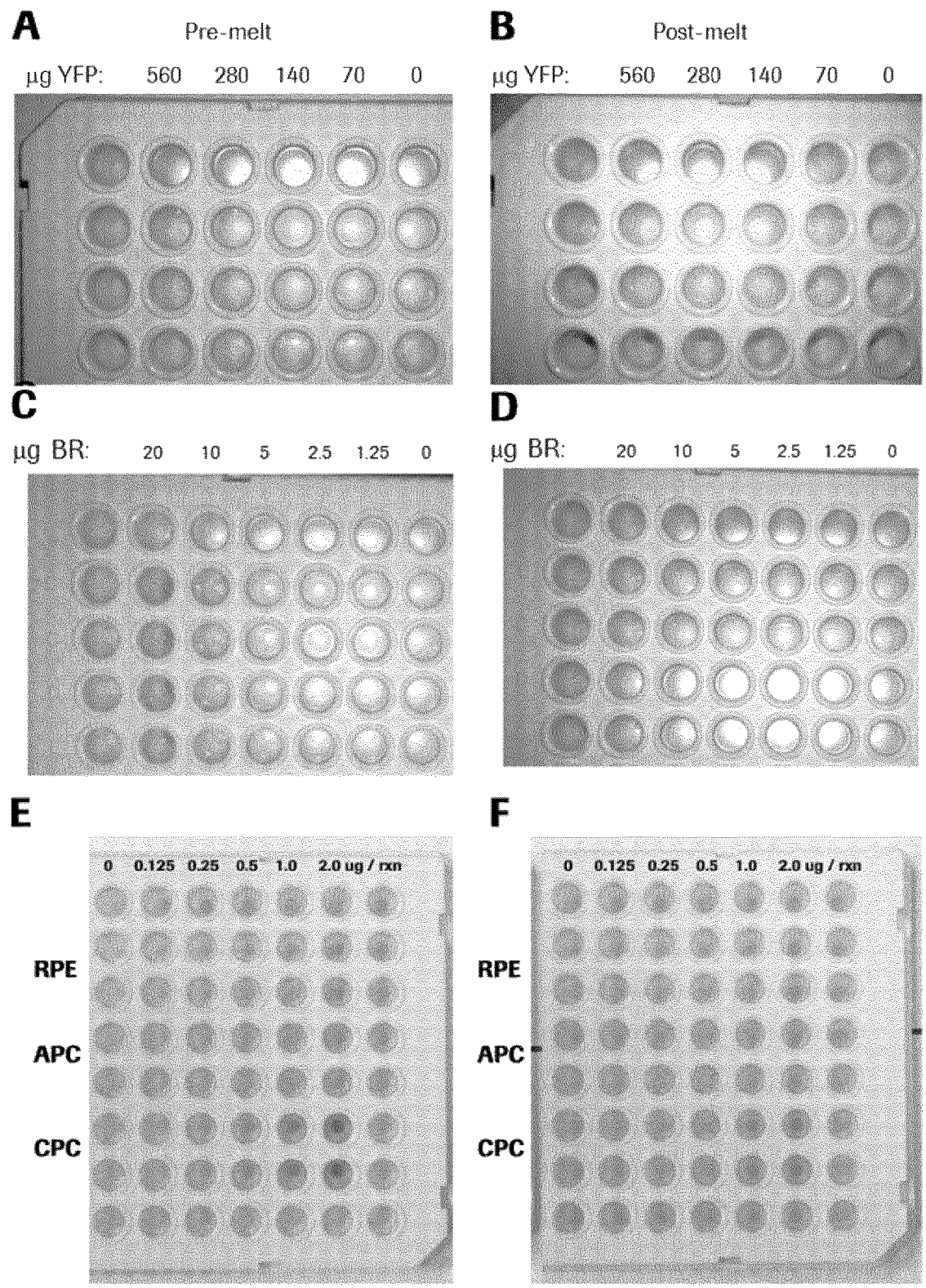
FIG. 1

Visualization and denaturation of thermolabile protein dyes in qPCR master mix.

A) Dilution series of YFP in 20 µL Roche Multiplex DNA Master imaged before denaturation.

B) The same plate as shown in Panel A imaged after 30 seconds at 95° C.

C) Dilution series of BR in 20 µL Roche Multiplex DNA Master imaged before denaturation. B) The same plate as shown in Panel C imaged after 30 seconds at 95° C.

D) Dilution series of the indicated phycobilliprotein in 20 µL Roche Multiplex DNA Master imaged before denaturation. B) The same plate as shown in Panel E imaged after 30 seconds at 95° C.

FIG. 2

Fluorescent/Absorbent properties of thermolabile visualization dyes in qPCR master mix. In the graphs, fluorescence intensity is represented by the y-axis, the x-axis represents incubation time.

A) YFP at 20 and 10 µg quantified in the 465-510 nm wavelength detection channel.

B) BR at 500 and 1000 µg measured as absorbance in the 533-610 nm wavelength detection channel.

C) Two-fold dilution series of R-PE from 2000 µg to 125 ng in the 533-580 nm wavelength detection channel.

D) Two-fold dilution series of APC from 2000 µg to 125 ng in the 618-660 nm wavelength detection channel.

E) Two-fold dilution series of C-PC from 2000 µg to 125 ng in the 618-660 nm wavelength detection channel.

FIG. 3

Duplex qPCR performance is not significantly affected by YFP or BR. In both graphs, fluorescence intensity is represented by the y-axis, the x-axis represents the number of PCR cycles.

A) FAM detection channel reaction quantifying beta-globin gene expression in the presence (green, blue curves) or absence (red) of the YFP/BR mixture. No template controls are shown in purple.

B) Px002 assay in the HEX detection channel from the same duplex reaction.

EXAMPLES

Example 1

The invention provides an aqueous composition comprising a purified thermostable polypeptide with biological activity, and a purified thermolabile water-soluble substance which in a functional conformation at a permissive temperature absorbs light and/or exhibits fluorescence, wherein the maximal permissive temperature of the polypeptide is above the maximal permissive temperature of the substance. For the selection of an exemplary thermolabile water-soluble substance, several candidate proteins visible to the human eye were tested. Particularly, their use as thermolabile visualization dye suitable for qPCR (quantitative polymerase chain reaction) master mixes was assessed.

According to the invention a thermolabile water-soluble substance as provided in the aqueous composition mentioned above allows the user to identify with ease all loaded wells in a standard 96- or 384-well assay plate. Because a thermolabile water-soluble substance as provided is denatured during the initial heating step of PCR or, in a specific embodiment, qPCR (quantitative PCR), such a dye will not interfere with fluorescent signals that may be generated in the course of DNA/RNA assays, especially real-time PCR assays. This technical effect is a distinguishing feature and a benefit over other loading and/or normalization dyes known to the art (e.g. Patent Blue V or Rox dyes). The emission spectra of dyes of the prior art either partially or wholly overlap with the target wave length of an instrument detection channel, needed for detecting fluorescent signals that may be generated in the course of PCR. Partial or complete overlap limit multiplexing in the process. Additionally, because in a specific embodiment a thermolabile water-soluble substance is a fluorescent protein, this property enables the thermocycler controlling software to automatically detect the loaded wells in a plate. In another embodiment, a specific DNA or RNA assay can be identified in a sample by using a 'barcode' combination of multiple thermolabile substances that are fluorescent and which can be detected individually in distinct detection channels of the thermocycler.

Example 2

Figure 2:
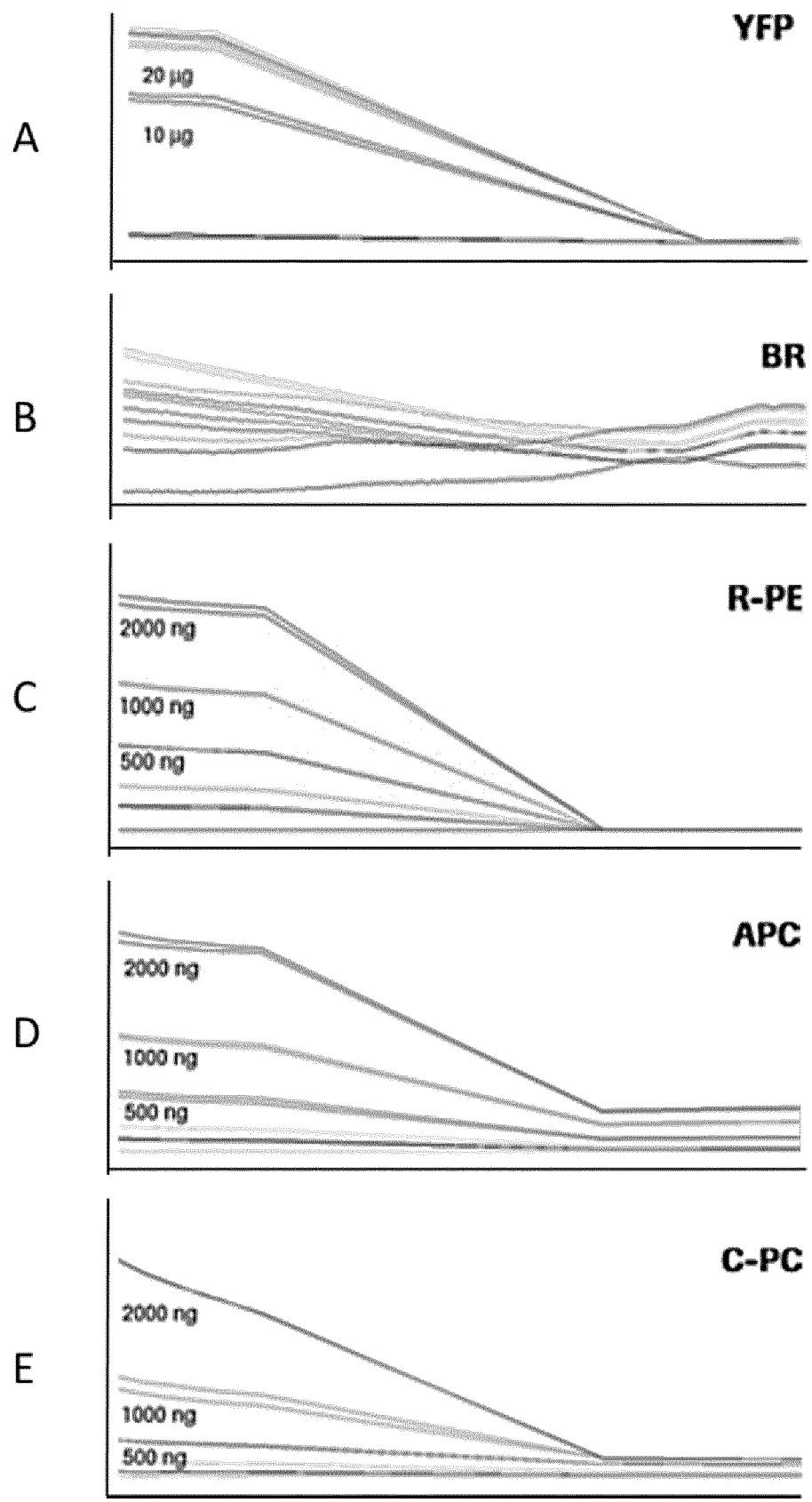
Figure 3:
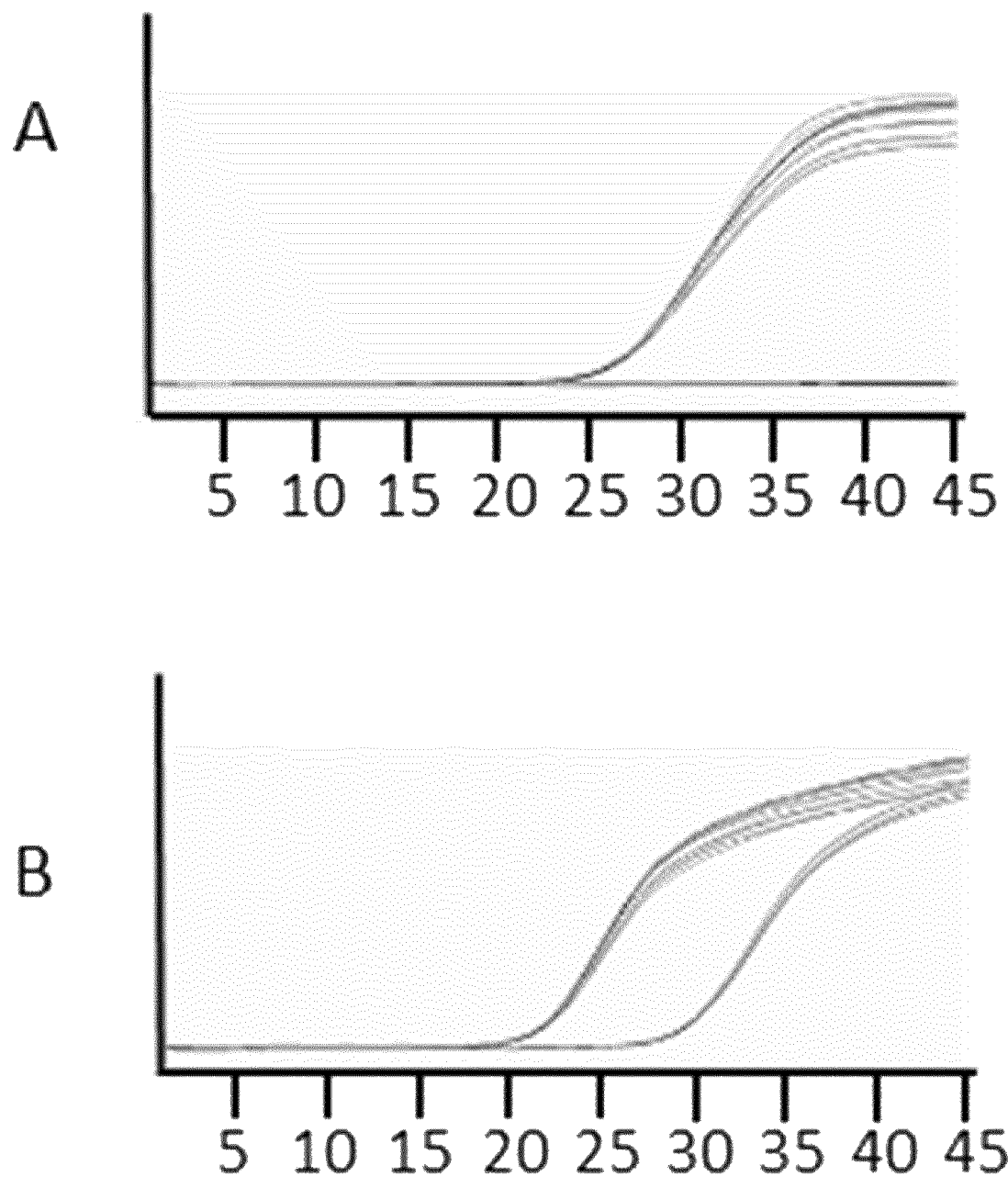

Exemplifying a thermolabile water-soluble substance in a composition according to the invention, three protein families were selected for investigation: green fluorescent protein (GFP) derived from *A. victoria*, bacteriorhodopsin (BR) from the halophilic archaebacterial *H. salinarum*, and phycobilliproteins like R-phycoerythrin (R-PE), allophycocyanin (APC), and c-phycocyanin (C-PC), which are isolated from deep sea algae. Initial work was performed using a dilution series of purified proteins in 20 µL reactions of Roche Multiplex DNA Master to determine the amount of visualization dye needed to see the mixture by eye. These reactions were then heated to 95° C. for 30 seconds to simulate the initial denaturation hold at the start of qPCR and gauge how completely the colored proteins were denatured under these conditions. FIG. 1 shows visualization of the dilution series and subsequent denaturation of reactions with yellow fluorescent protein (YFP), a mutant derivative of GFP. FIG. 2 illustrates the performance of BR under the same conditions, while FIG. 3 shows the results when R-PE, APC, or C-PC are used as visualization dyes.

All three protein families succeeded in visually distinguishing wells containing master mix with additive (the thermolabile water-soluble substance as indicator dye for presence of the master mix in the well) from wells without additive and empty wells. YFP required the most protein for visualization with a minimum of 140 µg needed in a 20 µL reaction to clearly see the yellow color (FIG. 1A) and when more than 200 µg of YFP was added, the color did not fully disappear with 30 seconds at 95° C. (FIG. 1B). With BR, visualization was achieved at levels between 2.5 and 5 µg (FIG. 1C) and the purple color effectively disappeared for all samples tested (FIG. 1D). Finally, the phycobilliproteins were clearly visible with just nanograms of protein added to the master mix: R-PE is seen with as little as 250-500 ng, APC is distinguishable between 500 and 1000 ng, and C-PC is distinctly blue down to the 500 ng level (FIG. 1E). For the phycobilliproteins in general, the color was denatured with the 95° C., 30 second heat pulse at levels below 1 µg.

Example 3

Next, the thermolabile properties of the candidate visual dyes were tested by fluorescence/absorbance on a Roche LightCycler 480 II qPCR instrument. Initial fluorescence of the dyes in 20 µL Multiplex DNA Master reactions was measured using filters appropriate for the specific target proteins: YFP (465-510 nm), BR (absorbance only, 533-610), R-PE (533-580), APC (618-660), and C-PC (618-660). As before, a 30 second hold at 95° C. was used to denature the protein dyes. FIG. 2 shows the results of these experiments. For reactions with either YFP (FIG. 2A) or R-PE (FIG. 2C) the fluorescence signal was reduced to baseline with the denaturation pulse. APC (FIG. 2D) and C-PC (FIG. 2E) saw a robust fluorescence signal reduced, but not eliminated by heating and while a trend of reduced absorbance was noted for BR (FIG. 2B), this signal was not clearly distinguishable from background noise.

Example 4

For all potential visual dye additives (i.e. thermolabile water-soluble substances as provided in an aqueous composition according to the invention) to DNA or RNA master mixes, qPCR performance must not be adversely affected by the presence of the dye additive. We first tested this with a blend of BR (7.5 µg) and YFP (200 ng) in 20 µL Multiplex DNA Master reactions. These reactions contained target template DNA and oligonucleotides for a duplex reaction, detecting beta-globin gene expression in the FAM channel and a synthetic transcript, Px002, in the HEX channel. FIG. 3 shows that this blend of visual dyes did not alter the Cp (crossing point) of the qPCR reactions or significantly affect the curve shape or plateau height, indicating equivalent performance in the presence or absence of BR and YFP at the levels tested. Similarly, we tested the R-PE additive at 400 ng with the same duplex assay in FIG. 4 and again, no effect on Cp, curve shape, or RFI plateau height were observed.

The invention claimed is:

1. An aqueous composition that is for polymerase chain reaction (PCR), said composition comprising a biologically active DNA polymerase that is thermostable up to at least 95° C. and a water soluble protein that absorbs light or exhibits fluorescence, wherein the water soluble protein is irreversibly denatured such that it cannot absorb light or exhibit fluorescence once the temperature of the composition is increased to 95° C.

2. The aqueous composition of claim 1, wherein the water soluble protein absorbs visible light.

3. The aqueous composition of claim 2, wherein the water soluble protein comprises a bacteriorhodopsin.

4. The aqueous composition of claim 3, wherein the bacteriorhodopsin is derived from *Halobacterium salinarum*.

5. The aqueous composition of claim 3, wherein the aqueous composition further comprises a chromophore.

6. The aqueous composition of claim 1, where the water soluble protein exhibits fluorescence.

7. The aqueous composition of claim 6, wherein the protein that that exhibits fluorescence is selected from the group consisting of Green Fluorescent Protein, Enhanced Green Fluorescent Protein, Yellow Fluorescent Protein, Blue Fluorescent Protein, Cyan Fluorescent Protein, Red Fluorescent Protein/R-Phycoerythrin, and Red Fluorescent Protein/dsRed.

* * * * *